United States Patent
Duranton et al.

(12) 
(10) Patent No.: US 6,203,783 B1
(45) Date of Patent: *Mar. 20, 2001

(54) USE OF ALKYL POLYGLYCOSIDES AND/OR OF O-ACYLATED DERIVATIVES OF GLUCOSE FOR TREATING HAIR LOSS

(75) Inventors: Albert Duranton; Isabelle Hansenne, both of Paris (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/709,666

(22) Filed: Sep. 9, 1996

Related U.S. Application Data

(63) Continuation of application No. 08/190,106, filed as application No. PCT/FR92/00773 on Aug. 5, 1992, now abandoned.

(30) Foreign Application Priority Data

Aug. 7, 1991 (FR) .................................................. 91 10060

(51) Int. Cl.$^7$ ................................ A61K 7/06; A61K 7/11; A61K 31/70
(52) U.S. Cl. ........................ 424/70.13; 424/70.1; 514/23; 514/25; 514/53
(58) Field of Search ................................ 424/70.1, 70.13; 514/23, 25, 53, 54, 61

(56) References Cited

FOREIGN PATENT DOCUMENTS

| 0357484 | 3/1990 | (EP) . |
| 0427210 | 5/1991 | (EP) . |
| 0428157 | 5/1991 | (EP) . |
| 2128627 | 5/1984 | (GB) . |

*Primary Examiner*—Theodore J. Criares
(74) *Attorney, Agent, or Firm*—Jacobson, Price, Holman & Stern, PLLC

(57) ABSTRACT

Cosmetic or pharmaceutical use of alkylpolyglycosides and/or O-acylated derivatives of glucose for treating hair loss. The compounds have the developed formula (II) where $R_1$ is a radical or a mixture of alkyl or alkenyl radicals; x is from 1 to 15 and/or compounds of the formula (III) where $R_2$ stands for a hydrocarbon chain and $R_3$ represents a $C_1$ to $C_4$ alkyl group or hydrogen; the compounds of the formula (II) not being used in the presence of pyrimidine derivatives.

18 Claims, No Drawings

USE OF ALKYL POLYGLYCOSIDES AND/OR OF O-ACYLATED DERIVATIVES OF GLUCOSE FOR TREATING HAIR LOSS

This application is a continuation of application Ser. No. 08/190,106, filed Jul. 7, 1994, now abandoned which is a 371 of PCT/FR92 filed Aug. 5, 1992.

The present invention relates to the use in cosmetics or in pharmacy of alkyl polyglycosides and/or of O-acylated derivatives of glucose for treating hair loss.

Hair growth and renewal are mainly determined by the activity of the hair follicles. Their activity is cyclic and essentially entails three phases, namely the anagen phase, the catagen phase and the telogen phase.

The active anagen phase, or growth phase, which lasts for several years during which the hair elongates, is succeeded by a very short and transient catagen phase and a rest phase, termed telogen phase, of a few months.

At the end of the rest period, the hair is shed and another cycle begins again. The head of hair is hence being constantly renewed in human beings and, of the approximately 150,000 hairs of which a head of hair is composed, approximately 10% are at rest at any instant and will hence be replaced in a few months.

In a large number of cases, early hair loss occurs in genetically predisposed subjects, and it affects men in particular. This applies, more especially, to androgenetic or androgenic or alternatively androgeno-genetic alopecia.

This alopecia is essentially due to a disturbance of hair renewal, which leads initially to an acceleration of the frequency of the cycles at the expense of the quality of the hairs, and then of their quantity. There is a gradual depletion of the head of hair through regression of so-called "terminal" hairs at the down stage. Some regions are affected preferentially, in particular the temporal or frontal areas in men, and a diffuse alopecia of the crown is observed in women.

Compositions that enable the effect of androgenetic alopecia to be abolished or reduced and, in particular, hair growth to be induced or stimulated or hair loss to be decreased have been sought for many years in the cosmetic or pharmaceutical industry.

In this connection, compounds such as 6-amino-1,2-dihydro-1-hydroxy-2-imino-4-piperidinopyrimidine or Minoxidil as well as its derivatives, as described in U.S. Pat. No. 4,139,619, have already been proposed.

Oligosaccharides containing at least one disaccharide unit consisting of a uronic acid residue and a hexosamine residue have also been proposed. They are described in European Patent Application EP 0,211,610.

The Applicant has just discovered, surprisingly, that alkyl polyglycoside compounds and/or O-acylated derivatives of glucose enabled hair growth to be induced and stimulated and hair loss to be decreased effectively.

The Applicant found, moreover, that the compositions containing these particular compounds displayed good stability on storage and improved cosmetic properties, especially in regard to sheen of the hair and deposition of powder thereon, and did not cause irritation of the scalp even after prolonged contact without rinsing.

A subject of the invention hence consists of the use in cosmetics of alkyl polyglycosides and/or of O-acylated derivatives of glucose for treating hair loss.

Another subject consists of the use of these compounds for the preparation of pharmaceutical compositions based on these particular compounds for the treatment of hair loss.

The subject of the invention is also a process for the cosmetic treatment of the hair and scalp by means of these compounds.

Other subjects will become apparent on reading the description and the examples which follow.

The use according to the invention employs compounds corresponding to the formula (I):

$$R_1(C_6H_{10}O_5)_xH \qquad (I)$$

corresponding to the structural formula (II):

(II)

[structural formula]

in which:

$R_1$ denotes an alkyl or alkenyl radical having an unbranched or branched $C_8$–$C_{24}$ chain, or a mixture of such radicals;

x is a number between 1 and 15;

and/or compounds corresponding to the formula (III):

(III)

[structural formula]

in which $R_2$ represents a saturated or unsaturated, linear hydrocarbon chain containing from 7 to 19 carbon atoms and $R_3$ represents hydrogen or a $C_1$–$C_4$ lower alkyl group; with the proviso that the compounds of formula (I) are not used in combination with pyrimidine derivatives.

The alkyl polyglycoside compounds of formula (I) as defined above, used according to the invention, are preferably represented by the products sold by the company HENKEL under the name APG, such as the products APG 300, APG 350, APG 500, APG 550, APG 625, APG base 10–12; the products sold by the company SEPPIC under the names TRITON CG 110 (or ORAMIX CG 110) and TRITON CG 312 (or ORAMIX NS 10); and those sold by the company BASF under the name LUTENSOL GD 70.

The compounds of formula (III) are known compounds, a process for the preparation of which is described below, and they are chosen, in particular, in the group of those in which the acyl residue $R_2$—CO— is an octanoyl, decanoyl, dodecanoyl, myristoyl, hexadecanoyl, stearoyl, oleoyl, linoleoyl or linolenoyl residue. By way of examples of compounds of formula (III), 6-O-oleoyl-D-glucose, 6-O-decanoyl-D-glucose, 6-O-dodecanoyl-D-glucose and 6-O-hexadecanoyl-D-glucose may be mentioned.

The general procedure for preparing D-glucose derivatives O-acylated at position 6, of formula (III), is as follows:

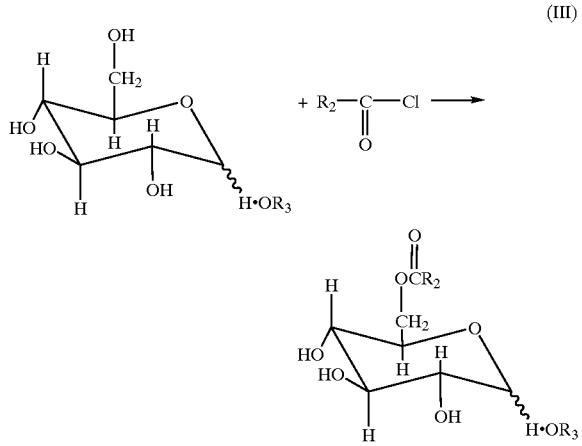

The synthesis is carried out using the chosen acid chloride and D-glucose according to the method described by E. REINEFELD et al., "Die Stärke", no. 6, pages 181–189, 1968.

The compounds according to the invention of formula (I) or (III) may be combined with compounds that further improve their activity with respect to hair regrowth and/or to the halting of hair loss, such as, more especially, the following compounds:

nicotinic acid esters including, more especially, $C_1$–$C_6$ alkyl nicotinates, and in particular methyl, hexyl and benzyl nicotinate, and the like;

steroidal and nonsteroidal anti-inflammatory agents which are well known in the prior art, and especially hydrocortisone, its salts and its derivatives, niflumic acid, and the like;

retinoids such as all-trans-retinoic acid also known as tretinoin, isotretinoin, retinol or vitamin A and its derivatives, for instance the acetate, palmitate or propionate, motretinide, etretinate and zinc all-trans-retinoate;

pyrimidine derivatives such as 6-amino-1,2-dihydro-1-hydroxy-2-imino-4-piperidinopyrimidine, also known under the name "minoxidil", as are described in U.S. Pat. No. 4,139,619, present only for the compounds of the formula (III);

antibacterial agents chosen from macrolides, pyranosides and tetracyclines, and erythromycin in particular;

calcium antagonists such as cinnarizine and diltiazem;

hormones such as estriol or analogs or thyroxine and its salts;

antiandrogens such as oxendolone, spironolactone and diethylstilbestrol;

OH radical trapping agents such as dimethyl sulfoxide.

It is also possible to combine with the compounds of the invention, optionally mixed with the others, compounds such as diazoxide corresponding to 3-methyl-7-chloro-[2H]-1,2,4-benzothiadiazine 1,1-dioxide; spiroxazone or 7-(acetylthio)-4', 5'-dihydrospiro[4-androstene-17,2'(3'H)-furan]-3-one; phospholipids such as lecithin; linoleic and linolenic acids, salicylic acid and its derivatives described in French Patent 2,581,542, such as salicylic acid derivatives bearing an alkanoyl group having 2 to 12 carbon atoms at position 5 of the benzene ring; hydroxycarboxylic or ketocarboxylic acids and their esters; lactones and their corresponding salts; anthralin; carotenoids; and icosatetraynoic and icosatriynoic acids or their esters and amides.

The compositions according to the invention containing these compounds can take the form of lotions, emulsions, creams or gels, and can be pressurized, where appropriate, as an aerosol. They may be applied, in particular, in treatments employing a composition as is defined above, the application of which is or is not followed by a rinse, or alternatively in the form of a shampoo.

In the nonrinsed compositions, the compounds of formula (I) or the compounds of formula (III) are present in proportions of between 0.1 and 10% by weight relative to the total weight of the composition, and preferably between 0.25 and 5% by weight.

In the compositions followed by a rinse, the same compounds are present in proportions of between 1 and 30% by weight relative to the total weight of the composition, and preferably between 5 and 15% by weight.

When the compositions according to the invention constitute a shampoo, they can contain anionic, nonionic, amphoteric or zwitterionic surfactants.

The medium used in these compositions can consist of water or a mixture of water and a solvent or a mixture of solvents, the solvents being chosen from organic solvents which are acceptable from a cosmetic standpoint, and more especially from $C_1$–$C_4$ lower alcohols; alkylene glycols; and alkylene glycol and dialkylene glycol alkyl ethers. The solvents, when they are present, occur in proportions of between 5 and 95% by weight relative to the total weight of the composition.

These compositions can contain other adjuvants customarily used in the cosmetic or pharmaceutical field for the purpose of producing topical compositions, such as surfactants, thickening agents, cosmetic agents such as, by way of a non-limiting example, polymers, proteins and, more especially, synthetic oils, preservatives or alkalinizing or acidifying agents. The pH of these compositions can vary between 3 and 9, and preferably between 5 and 8.

The thickening or gelling agents may be chosen from biopolysaccharides such as, for example, xanthan gums and scleroglucans, cellulose derivatives such as hydroxypropylcellulose and methylcellulose, polyacrylic acids, crosslinked or otherwise, polyethylene glycols and their derivatives, and combinations of anionic polymers and cationic polymers such as the combinations described in French Patent No. 2,598,611.

The thickeners are preferably present in proportions of between 0.1 and 5% by weight, and especially between 0.4 and 3% by weight, relative to the total weight of the composition.

The synthetic oils may be chosen from the following oils or mixtures thereof:

a) isoparaffins corresponding to the formula (1):

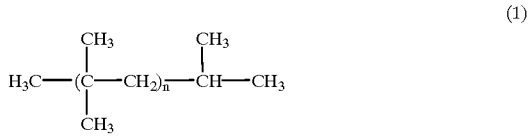

where n is between 2 and 16 inclusive;

b) a mixture of the isoparaffins of formula (1) with isoparaffins of formula (2):

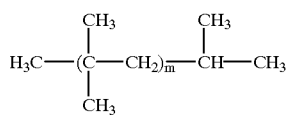

(2)

where m is equal to or greater than 18, and preferably between 18 and 40; the capillary viscosity of the oils defined under a) and b) being less than 500 cps [sic].

c) Polydecenes such as, for example, the products having viscosities at 40° C. of less than 40 cst [sic], sold by the company ETHYL CORPORATION under the names "ETHYLFLO 362 NF, 364 NF, 366 NF".

Among the synthetic oils corresponding to the formula (I [sic]) defined above, there may be mentioned those in which n is equal to 2, 3, 4 or 16, and especially the products sold under the names "PERMETHYL 99A, 101A, 102A or 104A" by the company PRESPERSE INC, or the product ARLAMOL HD sold by the company ICI, corresponding to the formula (I [sic]) in which n is equal to 3.

Among the synthetic oils of formula (II [sic]), there may be mentioned the product sold under the trade name "PERMETHYL 106A", corresponding to the formula (II [sic]) in which m is equal to 38.

The synthetic oils are present in proportions of between 0.05 and 20%, and preferably between 0.1 and 10%.

The process for treating hair loss consists mainly in applying a composition as defined above to the alopecic regions of an individual's scalp and hair, in leaving it in contact for several hours and, where appropriate, in rinsing.

It is possible, for example, to apply the composition to the hair and scalp at night, to keep the composition in contact all night long and, where appropriate, to carry out shampooing in the morning or to wash the hair using this composition and leaving the composition in contact again for a few minutes before rinsing.

The treatment process possesses the features of a cosmetic process inasmuch as it permits care of the hair and scalp in the cosmetic sense of the term, that is to say it enables them to be supplied with substances they lack and to be made more attractive.

The compositions according to the invention have proved especially advantageous when they are applied in the form of hair lotions, where appropriate rinsed, or of shampoos. In the form of shampoos, they display good foaming power.

The subject of the invention is also the use of the compounds of formula (I) or of the compounds of formula (III), as are defined above, for the preparation of a medicinal product intended for the treatment of scalp disorders such as alopecia, with the proviso that said medicinal product does not contain a pyrimidine derivative in the presence of compounds of formula (I) as defined above.

The examples which follow are intended to illustrate the invention, no limitation thereof being, however, implied.

Example 1

A nonrinsed lotion of the following composition is prepared:

| | |
|---|---:|
| Alkyl ($C_9/C_{10}/C_{11}$, 20:40:40) polyglycoside sold at an AS content of 50% under the name APG 300 by the company HENKEL | 3 g AS |
| Ethyl alcohol | 30.55 g |
| Perfume | qs |
| Water | qs 100 g |

Example 2

A shampoo of the following composition is prepared:

| | |
|---|---:|
| Alkyl ($C_{12}/C_{14}/C_{16}$, 68:26:6) polyglycoside sold at an AS content of 50% under the name APG 600 by the company HENKEL | 20 g AS |
| Hydroxypropylcellulose (MW 300,000) sold under the name KLUCEL G by the company AQUALON | 0.5 g |
| Ethyl alcohol | 50 g |
| Preservatives, perfume | qs |
| Water | qs 100 g |

Example 3

A nonrinsed lotion of the following composition is prepared:

| | |
|---|---:|
| Alkyl ($C_9/C_{10}/C_{11}$, 20:40:40) polyglycoside sold at an AS content of 50% under the name APG 300 by the company HENKEL | 5 g AS |
| Propylene glycol | 22.8 g |
| Ethyl alcohol | 55.1 g |
| Water | qs 100 g |

Example 4

A nonrinsed lotion of the following composition is prepared:

| | |
|---|---:|
| 6-O-Octanoyl-D-glucose | 5 g |
| Propylene glycol | 22.8 g |
| Ethyl alcohol | 55.1 g |
| Water | qs 100 g |

Example 5

A nonrinsed lotion of the following composition is prepared:

| | |
|---|---|
| 6-O-Oleoyl-D-glucose | 2.5 g |
| Propylene glycol | 22.8 g |
| Ethyl alcohol | 55.1 g |
| Water | qs 100 g |

Example 6

A nonrinsed lotion of the following composition is prepared:

| | |
|---|---|
| Alkyl ($C_{12}$—$C_{13}$) polyglycoside sold at an AS content of 50% under the name APG 500 by the company HENKEL | 5 g AS |
| propylene glycol | 22.8 g |
| Ethyl alcohol | 55.1 g |
| Water | qs 100 g |

Example 7

A nonrinsed lotion of the following composition is prepared:

| | |
|---|---|
| 6-O-Octanoyl-D-glucose | 2.5 g |
| Alkyl ($C_{12}$—$C_{13}$) glucoside sold at an AS content of 50% under the name APG 500 by the company HENKEL | 2.5 g AS |
| Propylene glycol | 22.8 g |
| Ethyl alcohol | 55.1 g |
| Water | qs 100 g |

Example 8

A shampoo for combating hair loss of the following composition is prepared:

| | |
|---|---|
| Alkyl ($C_9$/$C_{10}$/$C_{11}$, 20:40:40) polyglycoside sold at an AS content of 50% under the name APG 300 by the company HENKEL | 15 g AS |
| Xanthan gum sold under the name KELTROL T by the company RHONE POULENC | 1 g |
| Synthetic oil sold by the company ICI under the name ARLAMOL HD | 2 g |
| Preservative, perfume | qs |
| HCl | qs pH: 7 |
| Water | qs 100 g |

What is claimed is:

1. Process for treating hair loss, wherein at least one cosmetic composition comprising in a cosmetically acceptable medium at least one compound of formula:

$$R_1O(C_6H_{10}O_5)_xH \quad (I)$$

corresponding to the structural formula (II):

$$(II)$$

[structural formula II showing sugar ring with $R_1$—O—, $CH_2$—O—H, OH groups, with subscript x]

in which:
$R_1$ denotes an alkyl radical having an unbranched or branched $C_8$–$C_{24}$ chain, or a mixture of such radicals;
x is a number between 1 and 15;
and optionally at least one compound corresponding to the formula (III):

$$(III)$$

[structural formula III showing sugar ring with O—C(=O)—$R_2$, HO, OH, H·$OR_3$ groups]

in which $R_2$ represents a saturated or unsaturated, linear hydrocarbon chain containing from 7 to 19 carbon atoms and $R_3$ represents hydrogen or a $C_1$ to $C_4$ lower alkyl group is applied to the hair or scalp, said compound of formula (I) and said compound of formula (III) having hair regrowth activity and/or halting of hair loss activity.

2. Process according to claim 1, wherein the compounds of formula (III) are chosen from those for which the acyl radical $R_2$—CO— denotes an octanoyl, decanoyl, dodecanoyl, myristoyl, hexadecanoyl, stearoyl, olcoyl, linoleoyl or linolenoyl radical.

3. Process according to claim 1, wherein the composition contains, in addition, agents that improve the hair regrowth activity and/or the halting of hair loss activity of the compound of formula (I) or the compound of formula (III).

4. Process according to claim 3, wherein the agents that improve the hair regrowth activity and/or halting of hair loss activity are chosen from nicotinic acid esters, steroidal or nonsteroidal anti-inflammatory agents; retinoids; antibacterial agents; calcium antagonists; hormones; antiandrogens; or OH radical trapping agents.

5. Process according to claim 1, wherein the composition contains, in addition, 3-methyl-7-chloro-[2H]-1,2,4-benzothiadiazine 1,1-dioxide; 7-(acctylthio)-4'-5'-dihydrospiro-[4-androstene 17,2'(3H)-furan]-3-one; phospholipids; linoleic or linolenic acids; salicylic acid; salicylic acid derivatives bearing an alkanoyl group having 2 to 12 carbon atoms at position 5 of the benzene ring; hydroxycarboxylic or ketocarboxylic acids or their esters; lactones or their corresponding salts; anthralin; carotenoids; or icosatetraynoic or icosatriynoic acids or their esters or amides.

6. Process according to claim 1, wherein the composition is in the form of a lotion, emulsion, cream or gel.

7. Process according to claim 1, wherein the application of the composition is not followed by a rinse, and the compound of formula (I) and optionally the compound of formula (III) are contained in proportions of between 0.1 and 10% by weight relative to the total weight of the composition.

8. Process according to claim 1, wherein the application of the composition is followed by a rinse, and the compound of formula (I) and optionally the compound of formula (III) are contained in proportions of between 1 and 30% by weight relative to the total weight of the composition.

9. Process according to claim 1, wherein the cosmetically acceptable medium of the composition consists of water or a mixture of water and a cosmetically acceptable organic solvent.

10. Process according to claim 1, wherein the composition contains a solvent in proportions of between 5 and 95% by weight relative to the total weight of the composition.

11. Process according to claim 1, wherein the composition contains anionic, nonionic, amphoteric or zwitterionic surfactants; thickening agents, polymers, proteins, synthetic oils, preservatives, alkalinizing or acidifying agents or other adjuvants used in cosmetics or in pharmacy.

12. Process according to claim 1, wherein the composition contains thickening agents in proportions of between 0.1 and 5% by weight relative to the total weight of the composition.

13. Process according to claim 1, wherein the composition contains a synthetic oil or a mixture of synthetic oils in proportions of between 0.05 and 20% by weight relative to the total weight of the composition.

14. Process according to claim 13, wherein the synthetic oil of the composition is chosen from (a) the isoparaffins of formula:

$$H_3C-(\underset{\underset{CH_3}{|}}{\overset{\overset{CH_3}{|}}{C}}-CH_2)_{\overline{n}}-\underset{}{\overset{\overset{CH_3}{|}}{CH}}-CH_3$$

where n is between 2 and 16 inclusive;

(b) mixtures of isoparaffins of formula (1) with isoparaffins of formula:

$$H_3C-(\underset{\underset{CH_3}{|}}{\overset{\overset{CH_3}{|}}{C}}-CH_2)_{\overline{m}}-\underset{}{\overset{\overset{CH_3}{|}}{CH}}-CH_3$$

where m is equal to or greater than 18;

(c) polydecenes; or mixtures thereof.

15. Process according to claim 1, wherein the composition is pressurized in an aerosol device.

16. Process for treating hair loss, wherein at least a therapeutical composition comprising in a therapeutically acceptable medium at least one compound of formula:

$$R_1O(C_6H_{10}O_5)_xH \tag{I}$$

corresponding to the structural formula (II):

(II)

in which:
R$_1$ denotes an alkyl radical having an unbranched or branched C$_8$–C$_{24}$ chain, or a mixture of such radicals;
x is a number between 1 and 15;
and optionally at least one compound corresponding to the formula (III):

(III)

in which R$_2$ represents a saturated or unsaturated, linear hydrocarbon chain containing from 7 to 19 carbon atoms and R$_3$ represents hydrogen or a C$_1$ to C$_4$ lower alkyl group is applied to the hair or the scalp.

17. Process for the topical therapeutic treatment of hair loss comprising the application to the hair or scalp of a therapeutical composition including at least one compound of formula (III):

(III)

in which R$_2$ represents a saturated or unsaturated, linear hydrocarbon chain containing from 7 to 19 carbon atoms and R$_3$ represents hydrogen or a C$_1$ to C$_4$ lower alkyl group.

18. Process according to claim 17, wherein the hair and scalp are rinsed after the application of the therapeutical composition.

* * * * *